United States Patent
Lilliestråle et al.

(10) Patent No.: US 11,282,195 B2
(45) Date of Patent: *Mar. 22, 2022

(54) SYSTEM AND METHOD FOR CREATING A DECISION SUPPORT MATERIAL INDICATING DAMAGE TO AN ANATOMICAL JOINT

(71) Applicant: Episurf IP-Management AB, Stockholm (SE)

(72) Inventors: Richard Lilliestråle, Stockholm (SE); Anders Karlsson, Kävlinge (SE); Jeanette Spångberg, Skogäs (SE); Nina Bake, Lidingö (SE)

(73) Assignee: Episurf IP-Management AB, Stockholm (SE)

(*) Notice: Subject to any disclaimer, the term of this patent is extended or adjusted under 35 U.S.C. 154(b) by 0 days.

This patent is subject to a terminal disclaimer.

(21) Appl. No.: 16/886,650

(22) Filed: May 28, 2020

(65) Prior Publication Data
US 2020/0294232 A1 Sep. 17, 2020

Related U.S. Application Data

(63) Continuation of application No. 15/971,849, filed on May 4, 2018, now Pat. No. 10,672,124, which is a (Continued)

(30) Foreign Application Priority Data

Dec. 18, 2015 (EP) .................................. 15201361

(51) Int. Cl.
*G06T 7/00* (2017.01)
*G06T 7/13* (2017.01)
(Continued)

(52) U.S. Cl.
CPC ............ *G06T 7/0012* (2013.01); *A61B 6/466* (2013.01); *A61B 6/505* (2013.01); *A61B 6/5211* (2013.01);
(Continued)

(58) Field of Classification Search
CPC ............................ G06T 7/0012; G06F 19/345
See application file for complete search history.

(56) References Cited

U.S. PATENT DOCUMENTS 7,468,075 B2 12/2008 Lang et al.
7,664,297 B2 2/2010 Harada et al.
(Continued)

FOREIGN PATENT DOCUMENTS

EP 1139872 A2 10/2001
EP 1319217 A2 6/2003
(Continued)

OTHER PUBLICATIONS

Zohen et al., "Templates of the cartilage layers of the pate I lofe moral joint and their use in the assessment of osteoarthritic cartilage damage", 2003, OsteoArthritis and Cartilage (2003) 11, pp. 569-579 (Year: 2003).*

(Continued)

*Primary Examiner* — David F Dunphy
(74) *Attorney, Agent, or Firm* — Davis Wright Tremaine, LLP

(57) ABSTRACT

A system for creating decision support material indicating damage to an anatomical joint of a patient. The system is configured to: i) receive a series of radiology images of at least a part of the anatomical joint; ii) obtain a three-dimensional image representation of the at least part of the anatomical joint; iii) identify tissue parts of the anatomical joint using image analysis; iv) determine damage to the anatomical joint by analyzing said image representation; v)

(Continued)

mark damage to the anatomical joint in the obtained three-dimensional image representation; and vi) generate decision support material. The analysis comprises: detecting an irregular shape of a contour of a tissue part; and/or detecting that the intensity in an area within or adjacent to bone and/or cartilage parts differs from a predetermined value; and/or comparing at least one identified tissue part with a template representing a predefined damage pattern for an anatomical joint.

20 Claims, 8 Drawing Sheets

Related U.S. Application Data continuation of application No. 15/611,685, filed on Jun. 1, 2017, now Pat. No. 9,990,720, which is a continuation of application No. 15/382,523, filed on Dec. 16, 2016, now Pat. No. 9,697,601.

(51) Int. Cl.
*G06T 15/00* (2011.01)
*G06T 17/00* (2006.01)
*G06K 9/62* (2006.01)
*A61B 6/00* (2006.01)
*A61B 34/10* (2016.01)
*A61F 2/30* (2006.01)
*G16H 50/20* (2018.01)
*G16H 30/40* (2018.01)
*G16H 50/70* (2018.01)
*G16H 30/20* (2018.01)

(52) U.S. Cl.
CPC ............ *A61B 6/5217* (2013.01); *A61B 34/10* (2016.02); *A61F 2/30942* (2013.01); *G06K 9/6201* (2013.01); *G06K 9/6267* (2013.01); *G06T 7/13* (2017.01); *G06T 15/00* (2013.01); *G06T 17/00* (2013.01); *G16H 30/20* (2018.01); *G16H 30/40* (2018.01); *G16H 50/20* (2018.01); *G16H 50/70* (2018.01); *A61B 2034/102* (2016.02); *A61B 2034/105* (2016.02); *A61B 2034/107* (2016.02); *A61B 2034/108* (2016.02); *A61F 2/30756* (2013.01); *G06T 2207/10116* (2013.01); *G06T 2207/30008* (2013.01); *G06T 2207/30204* (2013.01)

(56) References Cited

U.S. PATENT DOCUMENTS

| | | | |
|---|---|---|---|
| 8,657,827 B2 | 2/2014 | Fitz et al. | |
| 2002/0087274 A1 | 7/2002 | Alexander et al. | |
| 2002/0147392 A1 | 10/2002 | Steines et al. | |
| 2002/0177770 A1 | 11/2002 | Lang et al. | |
| 2003/0216669 A1 | 11/2003 | Lang et al. | |
| 2004/0147927 A1 | 7/2004 | Tsougarakis et al. | |
| 2004/0153079 A1 | 8/2004 | Tsougarakis et al. | |
| 2004/0167390 A1 | 8/2004 | Alexander et al. | |
| 2005/0049524 A1 | 3/2005 | Lefevre et al. | |
| 2005/0054917 A1 | 3/2005 | Kitson | |
| 2005/0102315 A1 | 5/2005 | Krishnan | |
| 2007/0015995 A1 | 1/2007 | Lang et al. | |
| 2007/0203430 A1 | 8/2007 | Lang et al. | |
| 2007/0276224 A1 | 11/2007 | Lang et al. | |
| 2008/0015433 A1 | 1/2008 | Alexander et al. | |
| 2008/0195216 A1 | 8/2008 | Philipp | |
| 2008/0232658 A1 | 9/2008 | Sugaya et al. | |
| 2009/0076371 A1 | 3/2009 | Lang et al. | |
| 2009/0157083 A1 | 6/2009 | Park et al. | |
| 2009/0268956 A1 | 10/2009 | Wiley | |
| 2009/0270868 A1* | 10/2009 | Park | A61B 17/15 606/87 |
| 2009/0312805 A1 | 12/2009 | Lang et al. | |
| 2010/0023015 A1 | 1/2010 | Park | |
| 2010/0042105 A1 | 2/2010 | Park et al. | |
| 2010/0049195 A1 | 2/2010 | Park et al. | |
| 2010/0111837 A1* | 5/2010 | Boyden | A61K 9/0019 424/1.11 |
| 2010/0256479 A1 | 10/2010 | Park et al. | |
| 2010/0303313 A1 | 12/2010 | Lang et al. | |
| 2010/0303317 A1 | 12/2010 | Tsougarakis et al. | |
| 2010/0303324 A1 | 12/2010 | Lang et al. | |
| 2010/0305907 A1 | 12/2010 | Fitz et al. | |
| 2010/0329530 A1 | 12/2010 | Lang et al. | |
| 2011/0009964 A1 | 1/2011 | Schwartz et al. | |
| 2011/0054486 A1 | 3/2011 | Linder-Ganz et al. | |
| 2011/0087465 A1* | 4/2011 | Mahfouz | G16H 50/50 703/1 |
| 2011/0125003 A1* | 5/2011 | Reach | A61F 2/4657 600/407 |
| 2011/0125009 A1 | 5/2011 | Lang et al. | |
| 2011/0214279 A1 | 9/2011 | Park et al. | |
| 2011/0282473 A1* | 11/2011 | Pavlovskaia | G06F 19/00 700/98 |
| 2011/0295329 A1 | 12/2011 | Fitz et al. | |
| 2011/0295378 A1 | 12/2011 | Bojarski et al. | |
| 2012/0072183 A1 | 3/2012 | Lang et al. | |
| 2012/0143197 A1 | 6/2012 | Lang et al. | |
| 2012/0232670 A1 | 9/2012 | Bojarski et al. | |
| 2012/0265496 A1 | 10/2012 | Mahfouz | |
| 2012/0310347 A1 | 12/2012 | Linder-Ganz et al. | |
| 2012/0310400 A1 | 12/2012 | Park et al. | |
| 2013/0006598 A1 | 1/2013 | Alexander et al. | |
| 2013/0071828 A1 | 3/2013 | Lang et al. | |
| 2013/0110252 A1* | 5/2013 | Bake | A61F 2/30756 623/23.57 |
| 2013/0116788 A1 | 5/2013 | Schwartz et al. | |
| 2013/0123789 A1 | 5/2013 | Park | |
| 2013/0173228 A1 | 7/2013 | Bake et al. | |
| 2013/0184820 A1 | 7/2013 | Schwartz et al. | |
| 2013/0185927 A1 | 7/2013 | Bake et al. | |
| 2013/0336553 A1 | 12/2013 | Buisseret et al. | |
| 2013/0345845 A1 | 12/2013 | Park et al. | |
| 2014/0005792 A1 | 1/2014 | Lang et al. | |
| 2014/0005997 A1 | 1/2014 | Park et al. | |
| 2014/0029814 A1 | 1/2014 | Fitz et al. | |
| 2014/0039454 A1* | 2/2014 | Sharkey | A61B 17/1764 604/506 |
| 2014/0078139 A1 | 3/2014 | Park et al. | |
| 2014/0142643 A1 | 5/2014 | Bake et al. | |
| 2014/0249627 A1 | 9/2014 | Linder-Ganz et al. | |
| 2014/0257508 A1 | 9/2014 | Bojarski et al. | |
| 2014/0378978 A1 | 12/2014 | Park | |
| 2015/0120031 A1 | 4/2015 | Mahfouz | |
| 2015/0327795 A1 | 11/2015 | Alexander et al. | |
| 2015/0342739 A1 | 12/2015 | Mahfouz | |
| 2016/0000571 A1 | 1/2016 | Mahfouz | |
| 2016/0045317 A1 | 2/2016 | Lang et al. | |
| 2016/0199075 A1 | 7/2016 | Bake | |
| 2016/0228194 A1 | 8/2016 | Park et al. | |
| 2016/0228195 A1 | 8/2016 | Park et al. | |
| 2016/0228196 A1 | 8/2016 | Park et al. | |
| 2016/0228197 A1 | 8/2016 | Park et al. | |
| 2016/0270696 A1 | 9/2016 | Lang et al. | |
| 2016/0270856 A1 | 9/2016 | Park et al. | |
| 2016/0270857 A1 | 9/2016 | Park et al. | |
| 2016/0270858 A1 | 9/2016 | Park et al. | |
| 2016/0270859 A1 | 9/2016 | Park et al. | |
| 2016/0335776 A1* | 11/2016 | Maes | G06T 17/20 |
| 2016/0354092 A1 | 12/2016 | Park | |
| 2017/0000569 A1 | 1/2017 | Mahfouz | |
| 2017/0000614 A1 | 1/2017 | Mahfouz | |
| 2017/0000615 A1 | 1/2017 | Mahfouz | |
| 2017/0027701 A1 | 2/2017 | Mahfouz | |

(56) References Cited

U.S. PATENT DOCUMENTS

| | | | |
|---|---|---|---|
| 2017/0100253 A1* | 4/2017 | Bake | A61B 17/1604 |
| 2017/0172747 A1* | 6/2017 | Bake | A61F 2/30942 |

FOREIGN PATENT DOCUMENTS

| | | | |
|---|---|---|---|
| EP | 1322224 A1 | 7/2003 |
| EP | 1322225 A1 | 7/2003 |
| EP | 1389980 A2 | 2/2004 |
| EP | 1406203 A2 | 4/2004 |
| EP | 1450696 A1 | 9/2004 |
| EP | 1208410 B1 | 12/2004 |
| EP | 1558181 A1 | 8/2005 |
| EP | 2036495 A1 | 3/2009 |
| EP | 2114312 A2 | 11/2009 |
| EP | 2280671 A1 | 2/2011 |
| EP | 2291147 A1 | 3/2011 |
| EP | 2304645 A2 | 4/2011 |
| EP | 2319450 A1 | 5/2011 |
| EP | 2339991 A1 | 7/2011 |
| EP | 2389899 A1 | 11/2011 |
| EP | 2389905 A1 | 11/2011 |
| EP | 2400921 A1 | 1/2012 |
| EP | 2405865 A2 | 1/2012 |
| EP | 2470115 A1 | 7/2012 |
| EP | 2591756 A1 | 5/2013 |
| EP | 2765955 A1 | 8/2014 |
| EP | 3013256 A1 | 5/2016 |
| EP | 3075356 A1 | 10/2016 |
| EP | 2967813 A4 | 11/2016 |
| EP | 3102154 A1 | 12/2016 |
| EP | 3181050 A1 | 6/2017 |
| JP | H11104072 A | 4/1999 |
| JP | 2002532126 A | 10/2002 |
| JP | 2003144454 A | 5/2003 |
| JP | 2007268275 A | 10/2007 |
| JP | 200893229 A | 4/2008 |
| JP | 2010503503 A | 2/2010 |
| JP | 2010264230 A | 11/2010 |
| JP | 2014000425 A | 1/2014 |
| JP | 2014516630 A | 7/2014 |
| JP | 2017510307 A | 4/2017 |
| WO | 0035346 A2 | 6/2000 |
| WO | 0222013 A1 | 3/2002 |
| WO | 0222014 A1 | 3/2002 |
| WO | 0223483 A2 | 3/2002 |
| WO | 2002087444 A1 | 11/2002 |
| WO | 02096268 A2 | 12/2002 |
| WO | 03039377 A1 | 5/2003 |
| WO | 04043305 A1 | 5/2004 |
| WO | 08101090 A2 | 8/2008 |
| WO | 09154691 A2 | 12/2009 |
| WO | 10099231 A2 | 9/2010 |
| WO | 10099359 A1 | 9/2010 |
| WO | 10099360 A1 | 9/2010 |
| WO | 11147832 A1 | 12/2011 |
| WO | 11147837 A1 | 12/2011 |
| WO | 2012143628 A1 | 10/2012 |
| WO | 13052767 A1 | 4/2013 |
| WO | 13056036 A1 | 4/2013 |
| WO | 14145267 A1 | 9/2014 |
| WO | 14206498 A1 | 12/2014 |
| WO | 14207151 A1 | 12/2014 |
| WO | 2015117663 A1 | 8/2015 |
| WO | 16004992 A1 | 1/2016 |
| WO | 16005541 A1 | 1/2016 |
| WO | 2016004991 A1 | 1/2016 |
| WO | 2016005542 A1 | 1/2016 |
| WO | 2017103146 A1 | 6/2017 |

OTHER PUBLICATIONS

Birr et al., "The LiverAnatomyExplorer: A WebGL-Based Surgical Teaching Tool," IEEE Computer Graphics and Applications 33(5):48-58, published online May 2, 2013, print publication Sep. 1, 2013.

Dodin et al., "A fully automated system for quantification of knee bone marrow lesions using MRI and the osteoarthritis initiative cohort," Journal of Biomedical Graphics and Computing 3(1):51-65, Dec. 17, 2012, doi:10.5430/jbgc.v3n1p51.

Extended European Search Report dated Oct. 4, 2017, issued in EP Patent /Application No. 17176394.9, filed Dec. 18, 2015, 10 pages.

International Search Report and Written Opinion dated Jul. 26, 2018, International Patent Application No. PCT/EP2018/066012, filed Jun. 15, 2018, 14 pages.

International Search Report and Written Opinion dated Sep. 16, 2019, Patent Application No. PCT/EP2018/085055, filed Dec. 14, 2018, 14 pages.

Japanese Notice of Reasons for Refusal dated Jun. 25, 2019, Patent Application No. 2018-525771, filed Dec. 16, 2016, 5 pages.

Japanese Office Action dated Jan. 26, 2021, Patent Application No. 2019-561189, 6 pages.

Mühler et al., "The Medical Exploration Toolkit: An Efficient Support for Visual Computing in Surgical Planning and Training", IEEE Transactions on Visualization and Computer Graphics 16(1):133-146, Jan. 1, 2010.

Nielsen et al., "Measurement of bone marrow lesions by MR imaging in knee osteoarthritis using quantitative segmentation methods—a reliability and sensitivity to change analysis," BMC Musculoskeletal Disorders 15(447), Dec. 20, 2014, 11 pages, doi:10.1186/1471-2474-15-447.

\* cited by examiner

SYSTEM AND METHOD FOR CREATING A DECISION SUPPORT MATERIAL INDICATING DAMAGE TO AN ANATOMICAL JOINT

CROSS-REFERENCE TO RELATED APPLICATION

This application is a continuation of U.S. application Ser. No. 15/971,849, filed May 4, 2018, entitled "SYSTEM AND METHOD FOR CREATING A DECISION SUPPORT MATERIAL INDICATING DAMAGE TO AN ANATOMICAL JOINT," which is a continuation of U.S. application Ser. No. 15/611,685, filed Jun. 1, 2017, now issued as U.S. Pat. No. 9,990,720, entitled "SYSTEM AND METHOD FOR CREATING A DECISION SUPPORT MATERIAL INDICATING DAMAGE TO AN ANATOMICAL JOINT," which is a continuation of U.S. application Ser. No. 15/382,523, filed Dec. 16, 2016, now issued as U.S. Pat. No. 9,697,601, entitled "SYSTEM AND METHOD FOR CREATING A DECISION SUPPORT MATERIAL INDICATING DAMAGE TO AN ANATOMICAL JOINT," which claims benefit of EP Application No. 15201361.1, filed Dec. 18, 2015, the contents of which are incorporated by reference herein in their entirety.

TECHNICAL FIELD

The present disclosure relates generally to systems and methods for creating a decision support material indicating damage to at least a part of an anatomical joint of a patient.

BACKGROUND

In order to determine damage to an anatomical joint, it is common in medical practice today to use imaging techniques to depict the anatomical joint of interest and further to have a medical expert analyze the captured image data to determine whether there is damage. The medical expert then makes annotations about the conclusions drawn from the analysis of image data. The annotations are made available to a surgeon or orthopedic staff member who uses the annotations and the captured image data as a decision support for diagnosis and decision of suitable treatment of the patient.

However, this process is not very efficient as a manner of providing decision support, as only a fraction of the information that the medical expert in this way gathers when analyzing the image data, based on the knowledge of the medical expert, can be communicated in the present annotation format. Therefore, the decision support material received by the surgeon or orthopedic staff member is often inadequate.

Pierre Dodin et al: "A fully automated system for quantification of knee bone marrow lesions using MRI and the osteoarthritis initiative cohort", Journal of Biomedical Graphics and Computing, 2013, Vol. 3, No. 1, 20 Nov. 2012 describes an automated BML quantification method.

WO 2015/117663 describes a method of manufacturing a surgical kit for cartilage repair in an articulating surface of a joint in which a three dimensional image representation of a surface of the joint is generated.

Problems With The Prior Art

The method described in "A fully automated system for quantification of knee bone marrow lesions using MRI and the osteoarthritis initiative cohort" only detects bone marrow lesions, i.e. lesions in the cancellous bone—not even damage to the subchondral bone plate will be detected. This does not provide conclusive information regarding anything except the cancellous bone—it is not possible to draw definite conclusions regarding the cartilage status or the functioning of the joint. If there e.g. is a problem with just the cartilage, this will not be detected using the method described in the article. Further, it is not possible to judge the extent of the damage to a joint using just BML detection.

There is a need to address these problems of conventional methods and systems.

SUMMARY

The above described problems are addressed by the claimed system for creating a decision support material indicating damage to at least a part of an anatomical joint of a patient, wherein the created decision support material comprises one or more damage images. The system comprises a storage media and a processor which is configured to: i) receive a series of radiology images of the at least part of the anatomical joint from the storage media; ii) obtain a three-dimensional image representation of the at least part of the anatomical joint which is based on said series of radiology images by generating said three-dimensional image representation in an image segmentation process based on said radiology images, or receiving said three-dimensional image representation from the storage media; iii) identify tissue parts of the anatomical joint, including at least cartilage, tendons and/or ligaments, in at least one of the series of radiology images and/or the three-dimensional image representation using image analysis; iv) determine damage to the anatomical joint by analyzing at least one of the series of radiology images and/or the three-dimensional image representation of the at least part of the anatomical joint; v) mark damage to the anatomical joint in the obtained three-dimensional image representation of the at least part of the anatomical joint; and vi) generate a decision support material, where damage to the anatomical joint is marked in at least one of the one or more damage images of the decision support material, and at least one of the damage images is generated based on the obtained three-dimensional image representation of the at least part of the anatomical joint. The analysis of said at least one of the series of radiology images and/or the three-dimensional image representation of the at least part of the anatomical joint uses the identified tissue parts and comprises a selection of: detecting an irregular shape of a contour of at least one tissue part of the anatomical joint; and/or detecting that the intensity in an area within or adjacent to bone and/or cartilage parts of the anatomical joint is higher or lower than a predetermined value; and/or comparing at least one identified tissue part with a template representing a predefined damage pattern for an anatomical joint. The claimed system creates a decision support material, which clearly visualizes the extent of damage to the joint or a part of the joint, such as damage to the cartilage and underlying bone.

The series of radiology images may be captured during a process of radiology scanning through different layers of the anatomical joint or part of it, which captures all the radiology image data necessary to generate a three-dimensional image representation of the anatomical joint or part of it in an image segmentation process based on said radiology images.

The processor may be configured to identify bone parts and/or cartilage parts of the joint in the radiology image by detecting high contrast areas such as edges or contours in the radiology image, and identifying structures, such as bone and/or cartilage, in the radiology image through comparing the detected edges or contours with predefined templates.

The processor may, also or alternatively, be configured to associate the radiology images and the three-dimensional image representation, so that a marking made in one of the images appears in the same position in the other image. This simplifies the marking process.

The processor may, also or alternatively, be configured to select a suitable treatment from a predefined set of treatments based on data from the radiology images and/or the three-dimensional image representation of the at least part of the anatomical joint. The treatment may e.g. be the selection of a suitable implant from a predefined set of implants with varying dimensions, or the proposal of a transfer guide tool for graft transplantation, possibly including suitable size and/or suitable harvesting and/or implantation positions for osteochondral autograft plugs. In this case, the processor may further be configured to visualize the selected implant and/or the suitable transfer guide tool and/or the suitable harvesting and/or implantation positions for at least one osteochondral autograft plug in at least one of the one or more damage images.

The above described problems are also addressed by the claimed method for creating a decision support material indicating damage to at least a part of an anatomical joint of a patient, wherein the created decision support material comprises one or more damage images. The method comprises the steps of: i) receiving a series of radiology images of the at least part of the anatomical joint; ii) obtaining a three-dimensional image representation of the at least part of the anatomical joint which is based on said series of radiology images by generating said three-dimensional image representation in an image segmentation process based on said radiology images, or receiving said three-dimensional image representation from the storage media; iii) identifying tissue parts of the anatomical joint, including at least cartilage, tendons and/or ligaments, in at least one of the series of radiology images using image analysis; iv) determining damage to the anatomical joint by analyzing said at least one of the series of radiology images and/or the three-dimensional image representation of the at least part of the anatomical joint using the identified tissue parts and a selection of: detecting an irregular shape of a contour of at least one tissue part of the anatomical joint; and/or detecting that the intensity in an area within or adjacent to bone and/or cartilage parts of the anatomical joint is higher or lower than a predetermined value; and/or comparing at least one identified tissue part with a template representing a predefined damage pattern for an anatomical joint; v) marking damage to the anatomical joint in the obtained three-dimensional image representation of the at least part of the anatomical joint; and v) generating a decision support material, where the determined damage to the anatomical joint is marked in at least one of the one or more damage images of the decision support material, and at least one of the damage images is generated based on the obtained three-dimensional image representation of the at least part of the anatomical joint. The claimed method creates a decision support material, which clearly visualizes the extent of damage to the joint or a part of the joint.

The image analysis may identify bone parts and/or cartilage parts of the joint in the radiology image by the steps of detecting high contrast areas such as edges or contours in the radiology image, and identifying structures, such as bone and/or cartilage, in the radiology image through comparing the detected edges or contours with predefined templates.

The radiology images and the three-dimensional image representation may be associated so that a marking made in one of the images appears in the same position in the other image. This simplifies the marking process.

The method may further comprise selecting a suitable treatment from a predefined set of treatments based on data from the radiology images and/or the three-dimensional image representation of the at least part of the anatomical joint. The treatment may e.g. be the selection of a suitable implant from a predefined set of implants with varying dimensions, or the proposal of a transfer guide tool for osteochondral autograft transplantation, possibly including suitable size and/or suitable harvesting and/or implantation positions for osteochondral autograft plugs. In this case, the method may further comprise visualizing the selected implant and/or the suitable transfer guide tool and/or the suitable harvesting and/or implantation positions for at least one osteochondral autograft plug in at least one of the one or more damage images.

In the above described systems and methods, the image segmentation process may e.g. depend on a segmentation process control parameter set. If the image analysis identifies both bone parts and cartilage parts of the anatomical joint, damage may be determined to both the bone parts and the cartilage parts. The anatomical joint may be a knee, but may also be another joint such as an ankle, a hip, a toe, an elbow, a shoulder, a finger or a wrist. The decision support material may e.g. be adapted to be used by medical staff. It may include a recommendation for a suitable treatment for repair of the determined damage.

The above described problems are also addressed by a decision support material indicating damage to at least a part of an anatomical joint of a patient, wherein the decision support material comprises one or more damage images generated by the method steps of any one of the above described methods.

The above described problems are also addressed by a non-transitory machine-readable medium on which is stored machine-readable code which, when executed by a processor, controls the processor to perform any one of the above described methods.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Introduction

Figure 1:
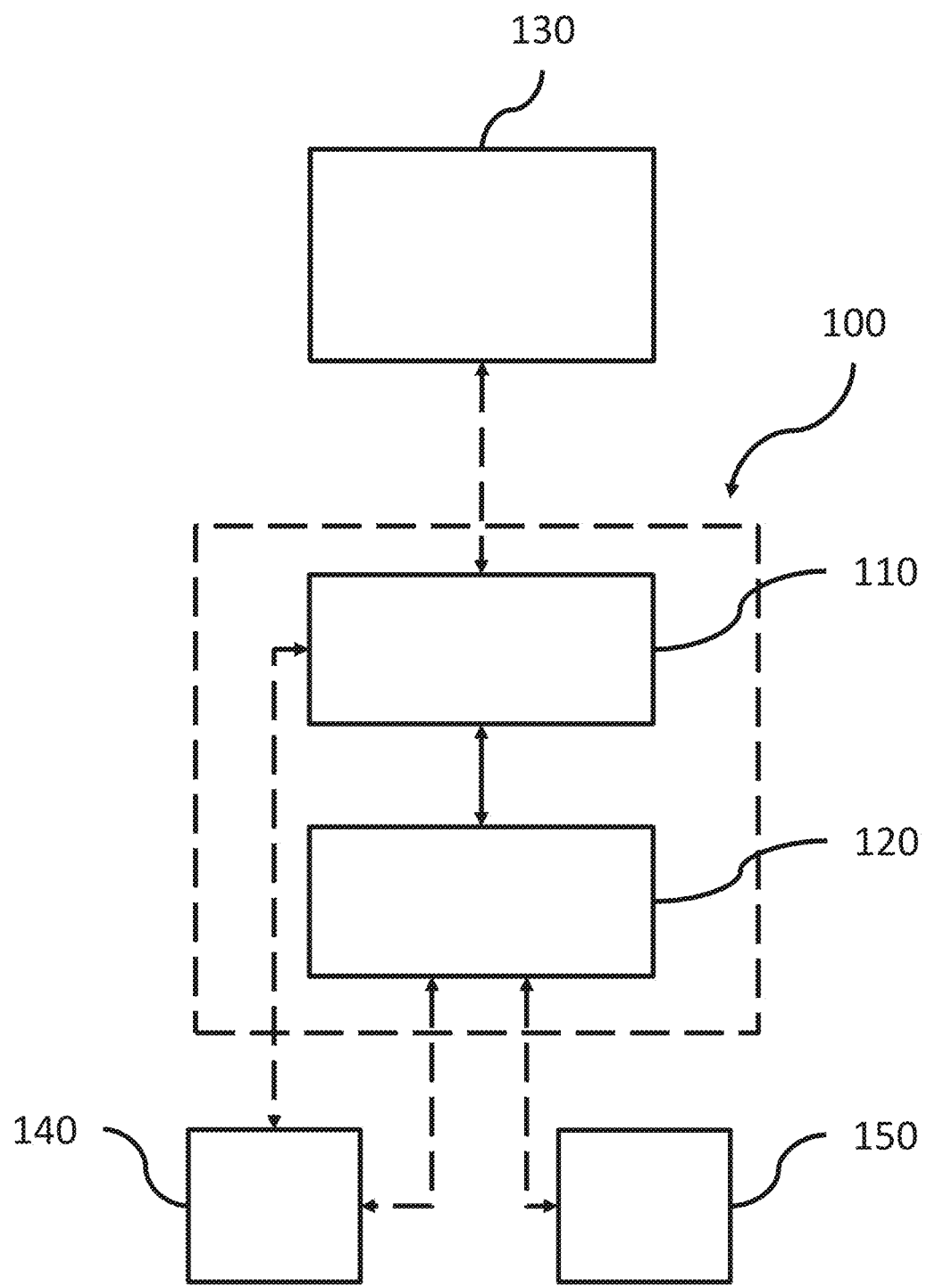
FIG. 1 shows a schematic view of a system for creating a damage image of at least a part of an anatomical joint, in accordance with one or more embodiments described herein.

The present disclosure relates generally to systems and methods for creating a decision support material indicating damage to at least a part of an anatomical joint of a patient.

More specifically, system and method embodiments presented herein provide an improved decision support material by creating one or more damage images of at least a part of an anatomical joint of a patient, wherein damage to the joint or a part of the joint is marked in at least one of the one or more damage images. In other words, there is provided one or more visualizations of a patient's joint together with indications/markings/visualization of its anatomical deviations, which forms a decision support for a surgeon or orthopedic staff member in deciding on an optimal treatment method, a decision support for an insurance agent making an assessment regarding a client or potential client, a decision support for a patient who wants to be informed about the condition of a damaged joint, or a decision support for any other person that has for example a commercial or academic interest in learning about damage to a depicted anatomical joint. This provides great advantages compared to conventional systems and methods, as much more information obtained from the medical image data is communicated, for example to the person making the decision on treatment of the patient. Thereby, embodiments of the invention solve the identified problems that the decision support material received by the surgeon or orthopedic staff member is many times inadequate as only a fraction of the information that a medical expert gathers when analyzing the image data, based on the knowledge of the medical expert, is communicated. In other words, using embodiments presented herein, an improved decision support material is obtained, which leads to more informed decisions being made on the optimal treatment of the patient whose anatomical joint is depicted in the decision support material.

In some embodiments, the anatomical joint is a knee, but the methods and systems presented herein may be used for deriving damage images of any suitable anatomical joint, e.g. an ankle, a hip, a toe, an elbow, a shoulder, a finger or a wrist. Damage need not be determined to a whole anatomical joint—often only a part of the joint is of interest, such as the femoral part of the knee joint.

In a non-limiting example, the anatomical joint is a knee and the damage/anatomical deviations that are determined and indicated/marked/visualized in the damage image are related to the femoral part of the knee joint, such as chondral and/or osteochondral lesions. In another non-limiting example, the anatomical joint is an ankle and the damage/anatomical deviations that are determined and indicated/marked/visualized in the damage image are related to the talus.

The damage image may comprise image data from a 2D representation of a generated 3D model of the anatomical joint, and/or comprise 2D image data retrieved directly from a digital imaging and communications in medicine (DICOM) file or any other suitable image file format. The 3D model may for example be generated based on a series of radiology images captured during a process of scanning radiology images through different layers of the anatomical joint or part of it, which captures all the radiology image data necessary to generate a 3D image representation of the anatomical joint or part of it in an image segmentation process based on said radiology images. A 3D model is advantageous for visualizing damage to bone, cartilage and other tissues. The DICOM format, or a comparable image file format, is advantageous for visualizing different parts of the anatomical joint.

For example, a 3D model may be used for visualizing bone and tissues such as cartilage, tendons and/or ligaments, and damages in relation to femoral knee bone and cartilage, or bone and cartilage of any other relevant anatomical joint that is being investigated. In another example, the DICOM format, or a comparable image file format, may be used for visualizing different parts of a knee, such as the femoral condyle and the trochlea area, or different parts of any other relevant anatomical joint that is being investigated, such as the talus of the ankle.

One or more damage images may be included in a damage assessment report that forms a decision support material to, for instance, facilitate for a surgeon or orthopedic staff member to make a correct diagnosis and decide on an optimal treatment of the patient. The one or more damage images, or the damage assessment report including the one or more damage images, do not include any diagnosis. Instead, they form a decision support for making a correct diagnosis and/or decide on an optimal treatment of the patient. The decision support material comprising one or more damage images, or a damage assessment report including one or more damage images, may for instance be used as a pre-arthroscopic tool, a digital version of standard arthroscopy to be used prior to an arthroscopy to give an arthroscopist a visual understanding of what he/she can expect to see. The decision support material may also be used as an alternative to arthroscopy, since enough information can often be gathered in this way without submitting the patient to an arthroscopy. The decision support material may in this case be used for planning the preferred treatment, such as an arthroplasty, a biological treatment such as a mosaicplasty of a microfracturing, or if a metal implant is needed.

In other examples, other types of users may receive and use the decision support material for different purposes. The decision support material, in the form of one or more damage images, or in the form of a damage assessment report including one or more damage images, may in different situations be of interest to medical staff, an insurance agent assessing a client or a potential client, a patient who wants to be informed about the condition of a damaged joint, or any other person who has for example a commercial or academic interest in learning about damage to a depicted anatomical joint. In different embodiments, the damage image or damage assessment report may be represented in printed form or in digital form. In digital form, the damage image, or the one or more damage images included in the damage assessment report, may be in static format or in a format allowing a user who is viewing a damage image on a display of a processing device to manipulate the image, by providing a control signal using an inputter connected to the processing device. The inputter may for example comprise a keyboard, a computer mouse, buttons, touch functionality, a joystick, or any other suitable input device.

In some embodiments, the decision support material may further include a recommendation and/or a position indication of a suitable implant for the determined bone and/or cartilage damage. In this context, a suitable implant means an implant having a type and dimensions that match a determined damage, thereby making it suitable for repairing the determined damage. Such a suitable implant may further be visualized in the damage image or damage report.

The decision support material may in some embodiments instead include a recommendation indicating a suitable transfer guide tool and/or suitable harvesting and/or implantation positions for at least one osteochondral autograft plug. The suitable transfer guide tool and/or the suitable harvesting and implantation positions may further be visualized in the damage image or damage report.

In some embodiments, the decision support material further indicates anatomical deviations which do not in themselves constitute damage to the joint. Such anatomical deviations may e.g. affect the choice of treatment for the determined damage. As a non-limiting example, severe osteophyte problems may indicate other problems, where an implant may not improve the situation.

The processor may in some embodiments comprise several different processors which together perform the claimed functions. In the same way, the storage media may in some embodiments comprise several different storage media which together perform the claimed functions.

System and method embodiments of the disclosed solution are presented in more detail in connection with the figures.

System Architecture

FIG. 1 shows a schematic view of a system 100 for creating a decision support material indicating damage to at least a part of an anatomical joint of a patient, the decision support material comprising one or more damage images. According to embodiments, the system comprises a storage media 110, configured to receive and store image data and parameters. In some embodiments, the system 100 is communicatively coupled, as indicated by the dashed arrow in FIG. 1, to an imaging system 130. The imaging system 130 may be configured to capture or generate radiology images, such as for example X-ray images, ultrasound images, computed tomography (CT) images, nuclear medicine including positron emission tomography (PET) images, and magnetic resonance imaging (MRI) images. The storage media 110 may be configured to receive and store radiology images and/or radiology image data from the imaging system 130.

The system 100 further comprises a processor 120 configured to, based on image data, determine damage in an anatomical joint, and create a damage image of the anatomical joint or a part of it where the determined damage to the joint is marked, or in other ways visualized, such that an observer of the damage image is made aware of the damage. The processor 120 may for example be a general data processor, or other circuit or integrated circuit capable of executing instructions to perform various processing operations.

In one or more embodiments, the processor is configured to: receive a series of radiology images of at least a part of the anatomical joint from the storage media; obtain a three-dimensional image representation of the at least part of the anatomical joint which is based on said series of radiology images by generating said three-dimensional image representation in an image segmentation process based on said radiology images, and/or receiving said generated three-dimensional image representation from the storage media; identify tissue parts of the anatomical joint, including at least cartilage, tendons and/or ligaments, in at least one of the series of radiology images, and/or the three-dimensional image representation, using image analysis; and determine damage to the anatomical joint by analyzing said radiology image and/or the three-dimensional image representation of the anatomical joint or part of it. The processor 120 may be configured to use the identified tissue parts and perform a selection of the following image analysis and processing operations:

detecting an irregular shape of a contour of at least one tissue part of the anatomical joint;

detecting that the intensity in an area within or adjacent to the bone and/or cartilage parts of the anatomical joint is higher or lower than a predetermined value; and/or comparing at least one identified tissue part with a template representing a predefined damage pattern for an anatomical joint.

The processor 120 is further configured to mark damage to the anatomical joint in the obtained three-dimensional image representation of the anatomical joint or part of it; and generate a decision support material where the determined damage to the anatomical joint is marked in at least one of the one or more damage images of the decision support material, and at least one of the damage images is generated based on the obtained three-dimensional image representation of the anatomical joint or part of it.

It may in some embodiments be advantageous to identify and analyze bone and cartilage of the depicted joint in the input radiology image/medical image data, as the combination of the two may provide additional information, but all embodiments described herein can also be performed when other tissues of the depicted joint are identified and analyzed.

In one or more embodiments, the processor 120 may be configured to identify bone parts and/or cartilage parts of the joint in the radiology image by detecting high contrast areas such as edges or contours in the radiology image. The processor 120 may further be configured to identify structures such as bone and/or cartilage in the radiology image by comparing detected edges or contours, and/or comparing intensity levels or patterns, with predefined templates.

As disclosed above, in one or more embodiments the processor 120 may be configured to, in the step of determining that there is damage by performing a selection of image analysis and processing operations, detect that the intensity in an area within or adjacent to the bone and/or cartilage parts of the anatomical joint is higher or lower than a predetermined threshold. Depending on the settings of the imaging device that has captured the analyzed medical image data, the analyzed image may for example represent the following substances with different intensity levels: cortical bone, fluid/liquids, cartilage, fat/bone marrow and meniscus. It is for example an indication of damage if fluid is detected where there in a healthy joint should be no fluid. If fluid is detected next to abnormalities in the cartilage, this can also be an indication of damage.

Different intensity levels in the analyzed image correspond to different signal intensity levels, and these may typically be represented by pixel/voxel values ranging from 0 to 1, or in a visual representation shown as grey scale levels from white to black. In embodiments where the pixel/voxel values range from 0 to 1, a predetermined threshold is set to a suitable value between 0 and 1, or in other words to a suitable grey scale value. In one or more embodiments the processor 120 may further, or alternatively, be configured to, in the step of performing a selection of image analysis and processing operations, detect an irregular shape of at least one tissue part of the anatomical joint and determine whether this represents a damage to the anatomical joint. In one or more embodiments the processor 120 may further, or alternatively, be configured to, in the step of performing a selection of image analysis and processing operations make a comparison of an identified tissue part in a damage image with a template representing a predefined damage pattern for an anatomical joint. In some embodiments, such a determination may include comparing a detected irregular shape of the contour with a template representing a predefined damage pattern for an anatomical joint, and/or comparing a detected intensity for a certain area with a template representing a predefined damage pattern for an anatomical joint.

In one or more embodiments, the processor 120 may be configured to mark, visualize or in another way indicate a determined damage to the anatomical joint in at least one of the one or more damage images of the decision support material. To mark, visualize or indicate the determined damage, the processor 120 may be configured to change the pixel/voxel value of one or more pixels/voxels on, in connection with, or surrounding a pixel/voxel identified to belong to a determined damage, such that the determined damage is visually distinguished and noticeable to a user/viewer, by performing a selection of the following:

changing the luminance/intensity values of one or more pixels/voxels identified as being located on a determined damage;

changing one or more chrominance/color values of one or more pixels/voxels identified as being located on a determined damage;

changing the luminance/intensity values of one or more pixels/voxels identified as surrounding a determined damage;

changing one or more chrominance/color values of one or more pixels/voxels identified as surrounding a determined damage; and/or adding an annotation, symbol or other damage indicator to the image, in connection with one or more pixels/voxels identified as being located on, or surrounding, a determined damage.

In one or more embodiments, the processor 120 may be configured to mark damage to the anatomical joint in the obtained three-dimensional image representation of the anatomical joint or part of it. To mark damage, the processor 120 may be configured to change the voxel value of one or more voxels on, in connection with, or surrounding a voxel identified to belong to a determined damage, such that the determined damage is visually distinguished and noticeable to a user/viewer, by performing a selection of the following:

changing the luminance/intensity values of one or more voxels identified as being located on a determined damage;

changing one or more chrominance/color values of one or more voxels identified as being located on a determined damage;

changing the luminance/intensity values of one or more voxels identified as surrounding a determined damage;

changing one or more chrominance/color values of one or more voxels identified as surrounding a determined damage; and/or adding an annotation, symbol or other damage indicator to the image, in connection with one or more voxels identified as being located on, or surrounding, a determined damage.

In one or more embodiments, the processor may be configured to synchronize, or associate, the series of radiology images and the three-dimensional (3D) image representation, so that a marking made in one of the images appear in real time in the same position in the other image. The same position is hereinafter interpreted as the same position, or same location, on the anatomical joint that is depicted. As the 3D image representation is generated based on the radiology image data, the synchronization or association between the 2D radiology image data and the 3D representation can be automatically performed by the processor during the segmentation of radiology image data into a 3D representation, in manners known in the art.

The series of radiology images may for example be captured during a process of scanning radiology images through different layers of the anatomical joint or part of it, which captures all the radiology image data necessary to generate a three-dimensional image representation of the anatomical joint or part of it in an image segmentation process based on the radiology images. In some embodiments, damage may be determined for both bone parts and cartilage parts of the anatomical joint. Alternatively, damage to bone parts only, or damage to cartilage parts only, or damage to other tissue parts, may be determined, depending on the application.

In some embodiments, the anatomical joint is a knee. In other embodiments, the anatomical joint may be any other anatomical joint suitable for damage determination using image data analysis, such as ankle, a hip, a toe, an elbow, a shoulder, a finger or a wrist.

In one or more embodiments, the processor may be configured to select a suitable treatment from a predefined set of treatments. The selection may be based on data from the radiology image and/or the three-dimensional image representation of the anatomical joint or part of it.

In some embodiments, the processor may be configured to select a suitable implant from a predefined set of implants with varying dimensions. In this context, a suitable implant means an implant having a type and dimensions that match a determined damage, thereby making it suitable for repairing the determined damage. In one or more embodiments, the processor may be configured to visualize the selected implant in at least one of the one or more damage images.

In some embodiments, the processor may be configured to propose a transfer guide tool for osteochondral autograft transplantation, possibly also including suitable size and/or suitable harvesting and/or implantation positions for at least one osteochondral autograft plug. In this context, a suitable harvesting position means a position where a suitable autograft plug can be harvested from the patient for repairing the determined damage.

In some embodiments, the decision support material is adapted to be used by medical staff, for example a surgeon or orthopedic staff member. The decision support material may then include a recommendation for a suitable treatment for repair of at least a part of the determined damage.

Alternatively, the decision support material includes a recommendation for a suitable design of one or more transfer guide tools for repair of at least a part of the determined damage with osteochondral autograft transplantation. The decision support material may in this case also include a recommendation for a suitable harvesting site for such an osteochondral autograft plug. Such suitable harvesting sites and/or transfer guide tools may further be visualized in the damage image or damage report.

In some embodiments, the damage image is part of a decision support material adapted to be used by an insurance agent making an assessment regarding a client or potential client; a patient who wants to be informed about the condition of a damaged joint; or any other person who has for example a commercial or academic interest in learning about damage to a depicted anatomical joint.

The decision support material may be in the form of a printed report, or in the form of one or more computer files adapted to be viewed on e.g. a tablet computer or a smart phone. If the decision support material is in the form of one or more computer files, the one or more damage images may be in the form of regular 2D images or in the form of an interactive 3D model of the anatomical joint or part of it.

In one or more embodiments, the system 100 may optionally comprise a display 140 configured to display image data, for example in the form of a damage image or a damage assessment report comprising one or more damage images. The display 140 may be configured to receive image data for display via the processor 120, and/or to retrieve image data for display directly from the storage media 110, possibly in response to a control signal received from the processor 120 or an inputter 150, which is further presented below.

In some embodiments, the system 100 may further optionally comprise one or more inputters 150 configured to receive user input. The inputter 150 is typically configured to interpret received user input and to generate control signals in response to said received user input. The display 140 and the inputter 150 may be integrated in, connected to or communicatively coupled to the system 100. The inputter 150 may for instance be configured to interpret received user input that is being input in connection with a displayed damage image, or a displayed damage assessment report comprising one or more damage images, and generate control signals in response to said received user input, to trigger display of an image or manipulation of image data being displayed, wherein the manipulations may be temporary or permanent. Such manipulations may for example include providing annotations, moving or changing an image or part of an image, changing the viewing perspective, zooming in or out, and/or any other suitable form of manipulation that enables the user to view and analyze the displayed image data in an improved manner. An inputter 150 may for example comprise a selection of a keyboard, a computer mouse, one or more buttons, touch functionality, a joystick, and/or any other suitable input device. In some embodiments, the processor 120 may be configured to receive a control signal from the inputter 150 and to process image data that is being displayed, or in other words manipulate a displayed image, in response to the received control signal.

The processor 120 may further be configured to perform the method steps of any or all of the embodiments presented herein.

Method Embodiments

Figure 2:
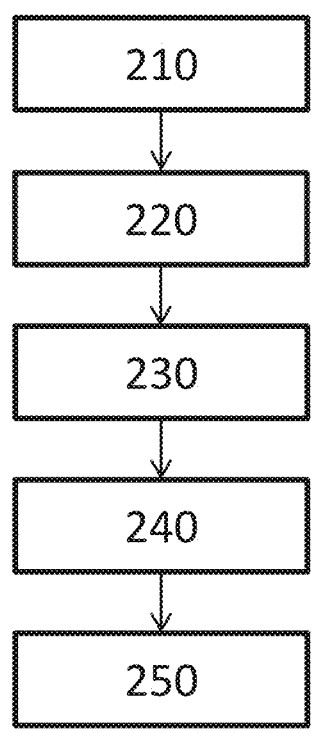
FIG. 2 is a flow diagram for a method for creating a damage image of at least a part of an anatomical joint, in accordance with one or more embodiments described herein.

FIG. 2 is a flow diagram of method embodiments for creating a decision support material indicating damage to at least a part of an anatomical joint of a patient, wherein the decision support material comprises one or more damage images. In accordance with one or more to embodiments, the method comprises:

In step 210: receiving a series of radiology images of the anatomical joint of a patient.

In some embodiments, the anatomical joint is a knee. In other embodiments, the anatomical joint may be any other anatomical joint suitable for damage determination using image data analysis, such as ankle, a hip, a toe, an elbow, a shoulder, a finger or a wrist.

In step 220: obtaining a three-dimensional image representation of the anatomical joint which is based on said series of radiology images by generating said three-dimensional image representation in an image segmentation process based on said radiology images, or receiving said three-dimensional image representation from a storage media.

In step 230: identifying tissue parts of the anatomical joint, including at least cartilage, tendons and/or ligaments, in at least one of the series of radiology images using image analysis.

In one or more embodiments, the image analysis identifies bone parts and/or cartilage parts of the joint in the radiology image by the steps of detecting high contrast areas such as edges or contours in the radiology image, and further identifying structures, such as bone and/or cartilage, in the radiology image through comparing the detected edges or contours with predefined templates.

In some embodiments, damage may be determined for both bone parts and cartilage parts of the anatomical joint.

It may in some embodiments be advantageous to identify and analyze bone and cartilage of the depicted joint in the input radiology image/medical image data, as the combination of the two may provide additional information, but all embodiments described herein can also be performed when only one of the substances bone and cartilage, or any other tissue part, of the depicted joint is being identified and analyzed.

In step 240: determining damage to the anatomical joint by analyzing the radiology image and/or the three-dimensional image representation of the anatomical joint or part of it.

In different embodiments, the analysis in step 230 may comprise performing a selection of any or all of the following image analysis and image processing operations:
  detecting an irregular shape of a contour of at least one tissue part of the anatomical joint; and/or
  detecting that the intensity in an area within or adjacent to bone and/or cartilage parts of the anatomical joint is higher or lower than a predetermined value; and/or
  comparing at least one identified tissue part with a template representing a predefined damage pattern for an anatomical joint.

In one or more embodiments, method step 240 may comprise detecting that the intensity in an area within or adjacent to the bone and/or cartilage parts of the anatomical joint is higher or lower than a predetermined threshold. Depending on the settings of the imaging device that has captured the analyzed medical image data, the analyzed image may for example represent the following substances with different intensity levels: cortical bone, liquids, cartilage, fat/bone marrow and meniscus. Different intensity levels in the analyzed image correspond to different signal intensity levels and these may typically be represented by pixel/voxel values ranging from 0 to 1, or in a visual representation shown as grey scale levels from white to black. In embodiments where the pixel/voxel values range from 0 to 1, a predetermined threshold is set to a suitable value between 0 and 1, or in other words to a suitable grey scale value.

In one or more embodiments, method step 240 may further, or alternatively, comprise detecting an irregular shape of a contour of the at least one tissue part of the anatomical joint and determine whether this represents a damage to the anatomical joint.

In one or more embodiments, method step 240 may further, or alternatively, comprise making a comparison of an identified tissue part in a damage image with a template representing a predefined damage pattern for an anatomical joint. In some embodiments, such a determination may include comparing a detected irregular shape of the contour with a template representing a predefined damage pattern for an anatomical joint, and/or comparing a detected intensity for a certain area with a template representing a predefined damage pattern for an anatomical joint.

In step 250: marking damage to the anatomical joint in the obtained three-dimensional image representation of the anatomical joint or part of it.

In step 260: generating a decision support material, where damage to the anatomical joint is marked in at least one of the one or more damage images of the decision support material, and at least one of the damage images is generated based on the obtained three-dimensional image representation of the anatomical joint or part of it.

It may in some embodiments be advantageous to identify, in step 230, and analyze, in step 240, both bone and cartilage of the depicted joint in the input radiology image/medical image data, as the combination of the two may provide additional information, but all embodiments described herein may also be performed when only one of the two substances bone or cartilage or any other tissue part of the depicted joint is identified and analyzed.

In one or more embodiments, the marking of method steps 250 and 260 comprises marking, visualizing or in another way indicating the determined damage to the anatomical joint. Marking, visualizing, or indicating the determined damage may include changing the pixel/voxel value of one or more pixels/voxels on, in connection with, or surrounding a pixel/voxel identified to belong to a determined damage, such that the determined damage is visually distinguished and noticeable to a user/viewer. Such a change of pixel/voxel values of one or more pixels/voxels on, in connection with, or surrounding a pixel/voxel identified to belong to a determined damage may for example comprise a selection of the following:

changing the luminance/intensity values of one or more pixels/voxels identified as being located on a determined damage;

changing one or more chrominance/color values of one or more pixels/voxels identified as being located on a determined damage;

changing the luminance/intensity values of one or more pixels/voxels identified as surrounding a determined damage;

changing one or more chrominance/color values of one or more pixels/voxels identified as surrounding a determined damage; and/or adding an annotation, symbol or other damage indicator to the image, in connection with one or more pixels/voxels identified as being located on, or surrounding, a determined damage.

In some embodiments, the radiology image and the three-dimensional image representation may be associated, or synchronized, so that a marking made in one of the images appear in the same position in the other image. According to one or more such embodiment, method steps 250 and 260 may comprise associating, or synchronizing, the radiology image and the three-dimensional image representation, so that a marking made in one of the images appear in the same position in the other image.

Figure 3:
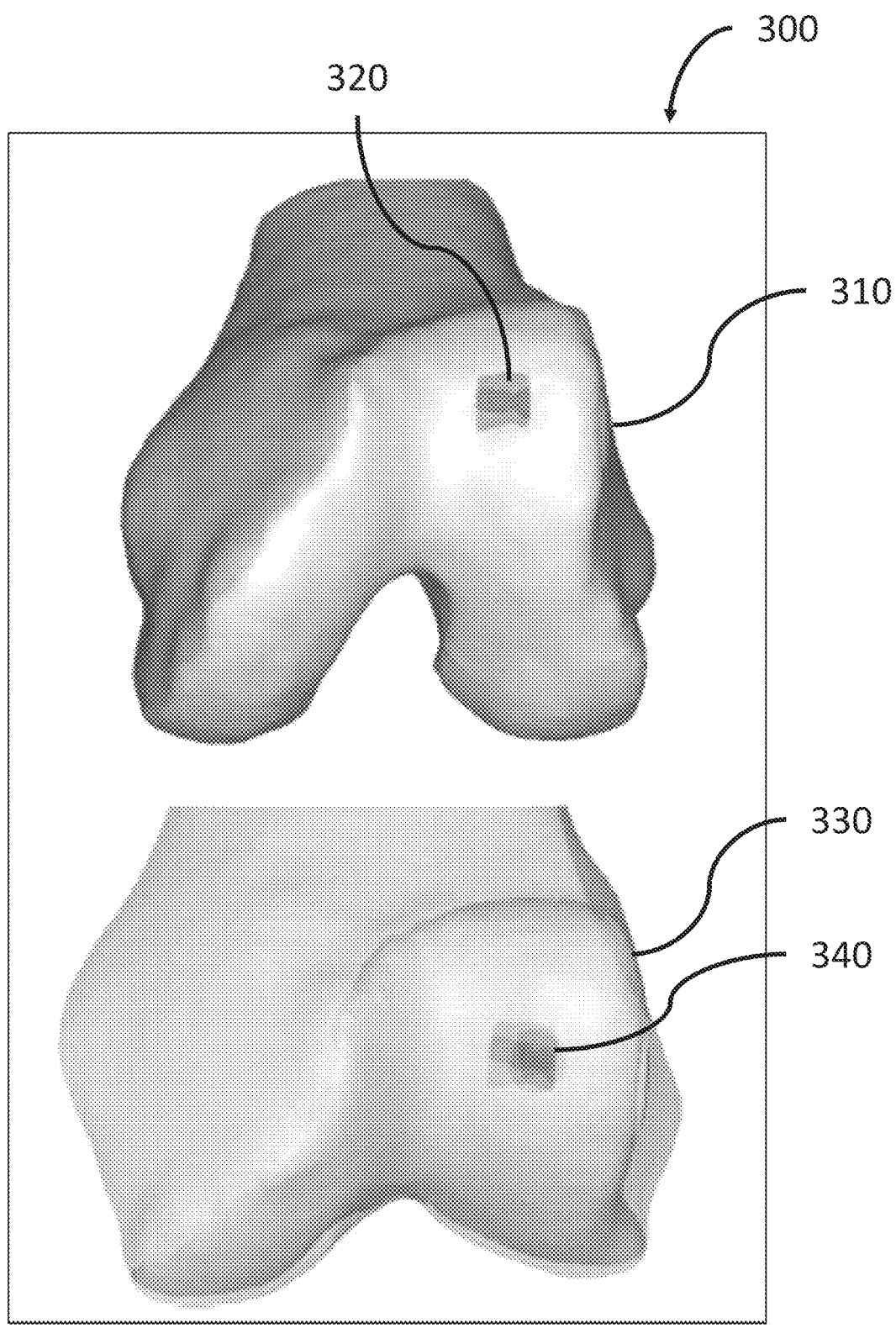
FIG. 3 shows an example of a decision support material in the form of a damage image wherein damage to an anatomical joint is marked using graphics, in accordance with one or more embodiments described herein.

FIG. 3 shows an example of a decision support material in the form of damage images wherein damage to an anatomical joint is marked using graphics, in accordance with one or more embodiments described herein. In the non-limiting example shown in FIG. 3, a decision support material 300 in the form of damage images shows two visual representations 310, 330 of an anatomical joint, wherein a determined damage 320, 340 is marked/indicated/visualized by changing the luminance/intensity levels and/or chrominance/color values of a number of pixels/voxels identified as being located on and surrounding a determined damage. Of course, any luminance/intensity values and/or chrominance/color values may be chosen, depending on the application, and depending on what provides a clear marking, visualization, or indication that enables a person viewing the decision support material to see and analyze the determined damage. A chosen luminance/intensity value and/or chrominance/color value may in embodiments be assigned to a pixel/voxel by replacing the previous pixel/voxel value, or by blending the new pixel/voxel values with the old pixel/voxel value using a scaling factor, such as an alpha blending factor. A single determined damage may further be marked, visualized, or indicated using different assigned pixel/voxel values depending on the type of damage that each pixel represents. As an example, marking, visualizing, or indicating a damage may comprise different new pixel/voxel values for:

a full-depth damage, i.e. a cartilage damage down to the bone;

a partial depth damage, such as degenerated cartilage, regenerated cartilage/scar tissue, or deformed cartilage;

a bone marrow lesion (BML); and a distinct cyst.

Figure 5:
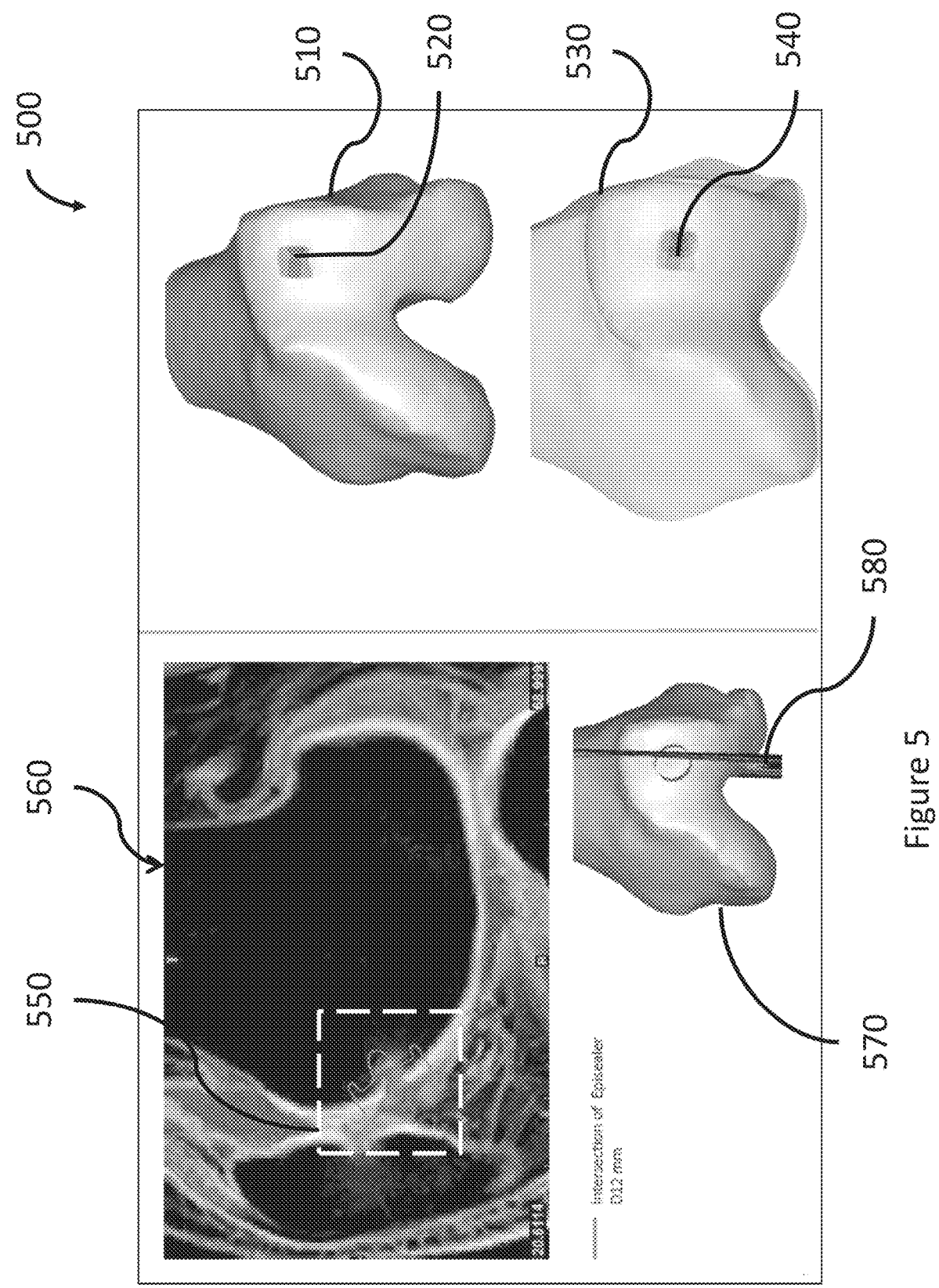
FIG. 5 shows an example of a decision support material in the form of a damage report comprising a number of damage images wherein damage to an anatomical joint is marked and/or a type and placement of a suitable implant is indicated, in accordance with one or more embodiments described herein.
Figure 6:
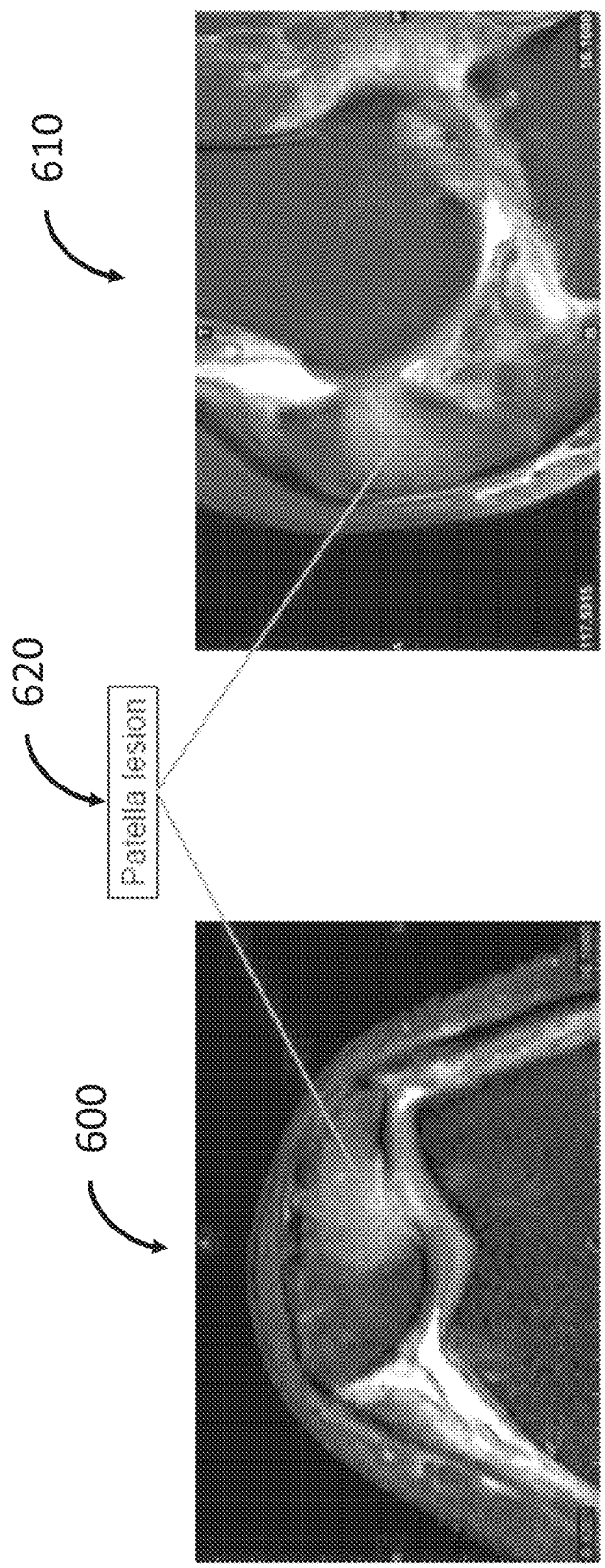
FIG. 6 shows an example of a decision support material in the form of a damage image wherein damage to an anatomical joint is marked using an annotation, in accordance with one or more embodiments described herein.

Examples of decision support material in the form of one or more damage images, or a damage report comprising one or more damage images, are discussed further in connection with FIGS. 5 and 6.

Figure 4:
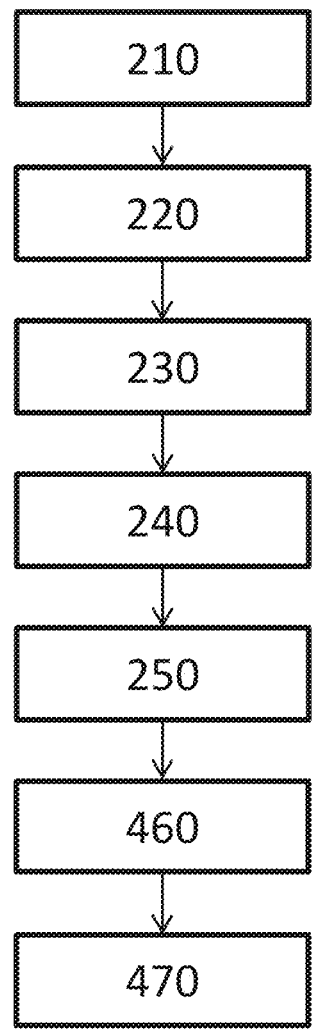
FIG. 4 is a flow diagram for a method for creating a damage image of at least a part of an anatomical joint, in accordance with one or more embodiments described herein.

FIG. 4 is a flow diagram of one or more method embodiments for creating a damage image of an anatomical joint where damage to the joint is marked in the damage image, and further the optional method steps of including in the image a recommendation of a suitable implant for repairing a determined damage. Steps 210-260 of FIG. 4 correspond to the same steps of FIG. 2, and the method embodiments of FIG. 4 further comprises the following additional steps:

In step 470: selecting a suitable implant from a predefined set of implants with varying dimensions, based on data from the radiology image and/or the three-dimensional image representation of the anatomical joint or part of it.

In this context, a suitable implant means an implant having a type and dimensions that match a determined damage, thereby making it suitable for repairing the determined damage.

In step 480: visualizing the selected implant in at least one of the one or more damage images.

In some embodiments, the decision support material may further include a recommendation and/or a position indication of a suitable implant for the determined bone and/or cartilage damage. Such a suitable implant may further be visualized in the damage image or damage report.

An example of how a selected implant may be visualized in a damage image or damage report is shown in FIG. 5, which shows an example of a decision support material 500 in the form of a damage report comprising a number of damage images 510, 530, 560, 570 wherein damage 520, 540 to an anatomical joint is marked and/or a type and placement of a suitable implant 550, 580 is indicated, in accordance with one or more embodiments described herein.

Figure 8:
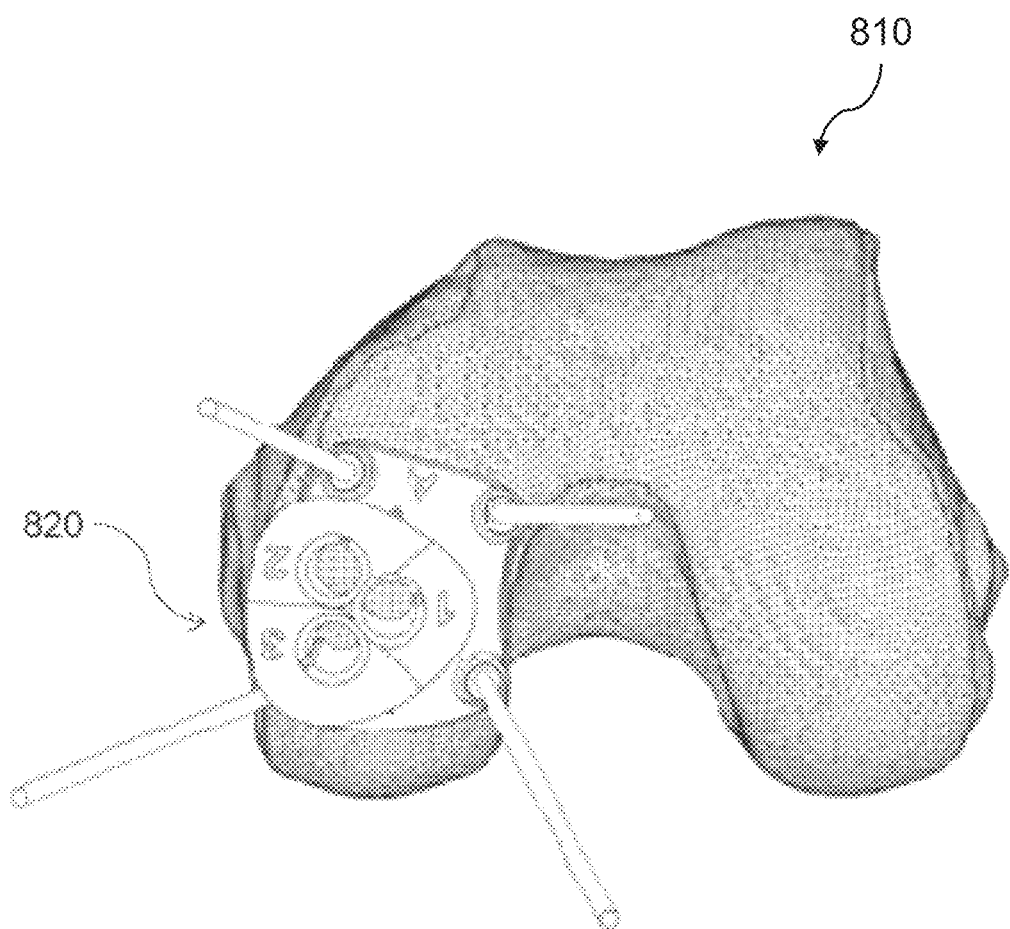
FIG. 8 shows an example of a damage image, in accordance with one or more embodiments described herein.

An example of the damage image may be used to visualize osteochondral autograft implantation is shown in FIG. 8, which shows an example of a damage image 810 in which the placement of a proposed transfer guide tool for osteochondral autograft transplantation is indicated in 820, in accordance with one or more embodiments described herein.

In one or more embodiments, the decision support material is adapted to be used by medical staff, for example a surgeon or orthopedic staff member. In one or more embodiments, the decision support material is adapted to be used by medical staff, for example a surgeon or orthopedic staff member, and further includes a recommendation for a suitable implant, according to any of the embodiments described in connection with FIG. 3.

In some embodiments, the decision support material is adapted to be used by an insurance agent making an assessment regarding a client or potential client; a patient who wants to be informed about the condition of a damaged joint; or any other person who has for example a commercial or academic interest in learning about damage to a depicted anatomical joint.

In some embodiments, the decision support material comprises a 2D and a 3D image representing a 3D visualization or 3D model of at least a part of an anatomical joint of a patient, visual marking/indication of a damage to the joint, and an annotation/a written assessment of anatomical deviations. FIG. 6 shows an example of a part of a decision support material comprising two damage images 600, 610, wherein damage to an anatomical joint that is depicted in the damage images 600, 610 is marked/indicated/visualized using an annotation 620, in accordance with one or more embodiments described herein. In the non-limiting example of FIG. 6, the depicted anatomical joint is a knee, and the annotation 620 indicates that the patient has a lesion in the patella.

In one or more embodiments, the methods of FIG. 2 or 4 may optionally comprise displaying a visual representation of a decision support material in the form of one or more damage images, or a damage assessment report comprising one or more damage images, for example in a graphical user interface (GUI). As shown in the non-limiting examples of FIGS. 3, 5 and 6, a visual representation presented in a GUI may comprise one or more damage images where damage to an anatomical joint is marked/visualized/indicted, for instance like the damage image 300 of FIG. 3, or a damage report comprising damage images along with a 2D representation and a 3D representation of the joint indicating a correct position of a recommended implant or guide tool, like the damage report 500 of FIG. 5, and/or medical image data wherein adding of annotations is enabled, like the annotation 620 added to indicate important medical information to the medical images 600 and 610 in FIG. 6. The method may in any of these embodiments comprise receiving image data for display, and/or receiving a control signal and retrieving image data for display in response to the control signal.

In one or more embodiments, a damage image or another part of a damage assessment report or decision support material that is being displayed may be manipulated by a user using one or more inputters integrated in, connected to, or communicatively coupled to the display or a system comprising the display. According to these embodiments, the method of FIG. 2 or 4 may further optionally comprise receiving user input from an inputter, interpret the received user input, and generate one or more control signals in response to the received user input. The received user input may relate to a displayed damage image, or a displayed damage assessment report comprising one or more damage images, and generate control signals in response to said received user input to manipulate what is being displayed, temporarily or permanently. The manipulation may for example include providing annotations, moving or changing an image or part of an image, changing the viewing perspective, zooming in or out, and/or any other suitable form of manipulation that enables the user to view and analyze the displayed image data in an improved manner. In some embodiments, the method of FIG. 2 or 4 may comprise receiving a control signal from an inputter and processing the image data that is being displayed, or in other words manipulate the displayed image, in response to the control signal.

The foregoing disclosure is not intended to limit the present invention to the precise forms or particular fields of use disclosed. It is contemplated that various alternate embodiments and/or modifications to the present invention, whether explicitly described or implied herein, are possible in light of the disclosure. Accordingly, the scope of the invention is defined only by the claims.

Use Case Embodiment

To set the presently disclosed methods and systems in a larger context, the damage marking and the generation of one or more damage images, and/or damage report, according to any of the disclosed embodiments, may in use case embodiments be preceded by capturing and/or obtaining medical image data representing an anatomical joint or part of it, and may further be followed by actions to be taken in view of repairing any determined damage.

Figure 7:
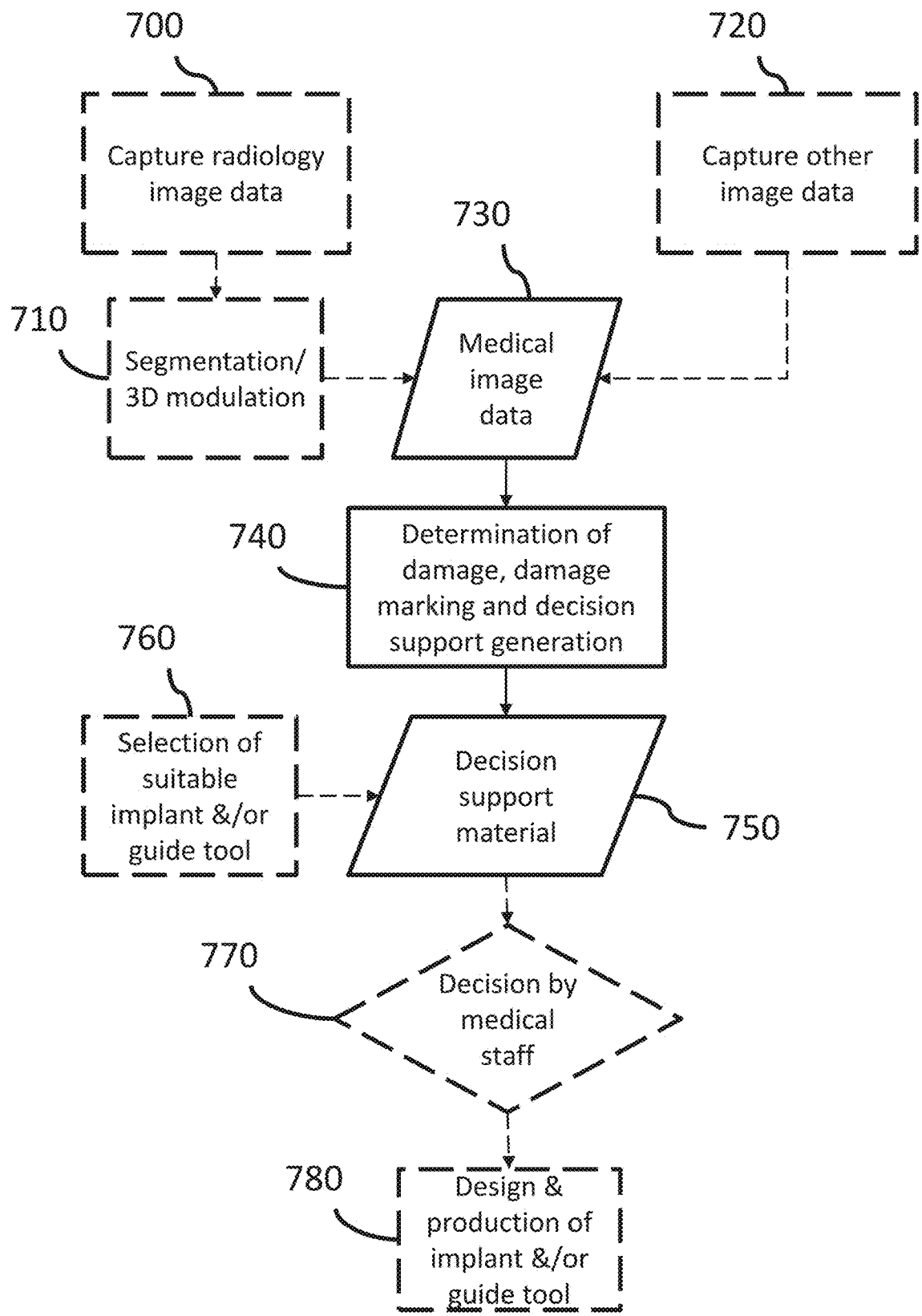
FIG. 7 is a flow diagram exemplifying the steps from obtaining medical image data to designing and producing an implant and/or guide tool for repair of a determined damage to an anatomical joint, including the steps of damage marking and generation of a damage marking image or report in accordance with one or more embodiments described herein.

FIG. 7 is a flow diagram exemplifying one such larger context, including obtaining medical image data from an image source, determining damage to a depicted anatomical joint and generating a damage image or damage report in accordance with one or more embodiments described herein. FIG. 7 further includes steps of designing and producing an implant and/or guide tool suitable for repairing a determined damage in an anatomical joint. In FIG. 7, everything except the determination of damage, damage marking and decision support material generation of step 740, using the input medical image data 730 and resulting in the output decision support material 740, is marked with dashed lines to clarify they are optional steps shown in the figure to provide context only, and not essential to any of the embodiments presented herein. Especially, steps 770 and 780 relating to diagnosis/decision on treatment and design and production of implant/guide tool are not part of the embodiments presented herein.

According to the example shown in FIG. 7, medical image data 730 may be obtained in a step 700 in the form of radiology image data from a radiology imaging system. The radiology image data obtained may for example be generated using one or more of a variety of imaging techniques such as X-ray images, ultrasound images, computed tomography (CT) images, nuclear medicine including positron emission tomography (PET) images, and magnetic resonance imaging (MRI) images. The radiology image data may for example be captured during a process of scanning radiology images through different layers of the anatomical joint or part of it, which captures all the radiology image data necessary to generate a three-dimensional image representation of the anatomical joint or part of it in an image segmentation process based on the radiology image data.

The image data obtained in step 400 may further be processed in a step 710, by performing segmentation and 3D modulation to obtain a 3D representation of what is depicted in the captured image data. For instance, if the image data captured depict an anatomical joint, the 3D representation would be a 3D representation of the anatomical joint. Medical image data may also be obtained in a step 720 from a different kind of image source that provides 2D image data. The 3D image data and the 2D image data both depict the same object, namely the anatomical joint of interest for damage determination. The medical image data 730 may therefore, as described herein, comprise 3D image data and/or 2D image data representing an anatomical joint, obtained using different imaging systems. The image data may represent only a part of the anatomical joint.

In embodiments where the medical image data 730 comprises both 3D and 2D image data, the 3D and 2D image data may be combined into a single visual representation, or be separate visual representations. The separate visual representations may in embodiments be associated, or synchronized, such that a position on an object depicted in the 3D visual representation is associated with the same position on the same object in the 2D visual representation. Thereby, if a marking of a determined damage is done in the 3D visual representation, it will appear on the same position on the depicted anatomical joint in the 2D representation, and vice versa. Of course, once the 3D and 2D visual representations have been associated, or synchronized, the same would apply to for example annotations placed in connection with a position of the depicted joint, or any modification done to the 3D or 2D visual representation.

In a step 740, damage determination, marking of damage in the input medical image data 730 and generation of the output decision support material 750 is performed, in accordance with any of the embodiments presented herein in connection with the method and system descriptions. The decision support material 750 may, in accordance with embodiments described herein, be in the form of one or more damage images wherein determined image to the depicted anatomical joint is marked, or in the form of a report comprising one or more such images. The decision support material 750 may optionally, in accordance with embodiments described herein, comprise an indication of one or more suitable implants and/or guide tools that may be used for repairing a determined damage. In this context, a suitable implant and/or guide tool means an implant and/or guide tool having a type and dimensions that match the determined damage, thereby making it suitable for repairing the determined damage. The one or more suitable implants and/or guide tools may be selected in the optional step 760, and may be presented graphically in connection with the 3D and/or 2D visual representation(s) of the marked medical image data of the decision support material 750, for example in the position where the implant and/or guide tool should optimally be inserted to repair the determined damage. Alternatively, the one or more suitable implants and/or guide tools may be selected in the optional step 470 and may be presented separated from the 3D and/or 2D visual representations for example as a graphical representation and/or a text annotation.

In a use case embodiment, a medical staff member, for example a surgeon or orthopedic staff member, may use a generated decision support material 750 to make a correct diagnosis and make a decision 770 on an decision of optimal treatment of the patient whose anatomical joint has been depicted. If the medical staff member decides that an implant is required, this may lead up to the step 780 of designing and producing a suitable implant and/or guide tool, possible according to an indication that may be provided in the decision support material, as described herein, for repairing the determined damage.

In another use case embodiment, a person using the decision support material 750 may be a person other than a medical staff member that has an interest in learning about any damage to the depicted anatomical joint, for example an insurance agent assessing a client or a potential client, a patient who wants to be informed about the condition of a damaged joint, or any other person who has for example a commercial or academic an interest in learning about any damage to a depicted anatomical joint.

Further Embodiments

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the claimed scope of the present disclosure. Where applicable, the various hardware components and/or software components set forth herein can be separated into sub-components comprising software, hardware, or both without departing from the claimed scope of the present disclosure. In addition, where applicable, it is contemplated that software components can be implemented as hardware components, and vice-versa. The method steps of one or more embodiments described herein may be performed automatically, by any suitable processing unit, or one or more steps may be performed manually. Where applicable, the ordering of various steps described herein can be changed, combined into composite steps, and/or separated into sub-steps to provide features described herein.

Software in accordance with the present disclosure, such as program code and/or data, can be stored in non-transitory form on one or more machine-readable mediums. It is also contemplated that software identified herein can be implemented using one or more general purpose or specific purpose computers and/or computer systems, networked and/or otherwise.

In embodiments, there are provided a computer program product comprising computer readable code configured to, when executed in a processor, perform any or all of the method steps described herein. In some embodiments, there are provided a non-transitory computer readable memory on which is stored computer readable and computer executable code configured to, when executed in a processor, perform any or all of the method steps described herein.

In one or more embodiments, there is provided a non-transitory machine-readable medium on which is stored machine-readable code which, when executed by a processor, controls the processor to perform the method of any or all of the method embodiments presented herein.

The invention claimed is:

1. A system for creating a decision support material indicating damage to at least a part of an anatomical joint of a patient, wherein the created decision support material comprises one or more damage images, the system comprising a storage media and at least one processor, wherein the at least one processor is configured to:
   i) receive a series of radiology images of the at least part of the anatomical joint from the storage media;
   ii) obtain a three-dimensional image representation of the at least part of the anatomical joint which is based on at least a part of said series of radiology images, by generating said three-dimensional image representation in an image segmentation process based on said series of radiology images, or receiving said three-dimensional image representation from a storage media;
   iii) identify tissue parts of the anatomical joint in at least one of at least a part of said series of radiology images and/or the three-dimensional image representation using image analysis;
   iv) determine damage to the identified tissue parts in the anatomical joint by analyzing at least one of at least a part of said series of radiology images and/or the three-dimensional image representation of the at least part of the anatomical joint;
   v) mark damage to the anatomical joint in the obtained three-dimensional image representation of the anatomical joint; and
   vi) generate a decision support material, where the determined damage to the at least part of the anatomical joint is marked in at least one of the one or more damage images of the decision support material, and at least one of the one or more damage images is generated based on the obtained three-dimensional image representation of the at least part of the anatomical joint.

2. The system according to claim 1, wherein at least one of the one or more damage images is an interactive 3D model of the anatomical joint or part of it.

3. The system according to claim 1, wherein the processor is configured to identify bone parts and/or cartilage parts of the joint in said at least one radiology image by:
   detecting high contrast areas such as edges or contours in the radiology image; and
   identifying structures, such as bone and/or cartilage, in the radiology image through comparing the detected areas with predefined templates.

4. The system according to claim 1, wherein the processor is configured to determine damage to the identified tissue parts in the anatomical joint by:
   detecting an irregular shape of a contour of at least one tissue part of the anatomical joint; or
   detecting that the intensity in an area within or adjacent to bone and/or cartilage parts of the anatomical joint is higher or lower than a predetermined value; or
   comparing at least one identified tissue part with a template representing a predefined damage pattern for an anatomical joint.

5. The system according to claim 1, wherein the processor is further configured to associate the radiology images and the three-dimensional image representation, so that a marking made in one of the images appears in the same position in another image.

6. The system according to claim 1, wherein the anatomical joint is an ankle, and the damage that is determined and marked in at least one of the one or more damage images of the decision support material is related to the talus.

7. The system according to claim 1, wherein the image analysis identifies both bone parts and cartilage parts of the anatomical joint or part of it and damage is determined to both the bone parts and the cartilage parts.

8. The system according to claim 1, wherein the processor is configured to:
   select a suitable implant from a predefined set of implants with varying dimensions, and/or propose a transfer guide tool for osteochondral autograft transplantation, possibly including suitable size and/or suitable harvesting and/or implantation positions for at least one osteochondral autograft plug based on data from the radiology images and/or the three-dimensional image representation of the at least part of the anatomical joint; and to
   visualize the selected implant and/or the transfer guide tool and/or the suitable harvesting and/or implantation positions for at least one osteochondral autograft plug in at least one of the one or more damage images.

9. The system according to claim 1, wherein the decision support material is adapted to be used by medical staff, and includes a recommendation for a suitable treatment for repair of the determined damage.

10. A method for creating a decision support material indicating damage to at least a part of an anatomical joint of a patient, wherein the created decision support material comprises one or more damage images, the method comprising the steps of:
    i) receiving a series of radiology images of the at least part of the anatomical joint;
    ii) obtaining a three-dimensional image representation of the at least part of the anatomical joint which is based on at least a part of said series of radiology images, by generating said three-dimensional image representation in an image segmentation process based on said radiology images, or receiving said three-dimensional image representation from a storage media;
    iii) identifying tissue parts of the anatomical joint in at least one of at least a part of said series of radiology images using image analysis;
    iv) determining damage to the identified tissue parts in the anatomical joint by analyzing at least one of the at least a part of said series of radiology images and/or the three-dimensional image representation of the at least part of the anatomical joint;
    v) marking damage to the anatomical joint in the obtained three-dimensional image representation of the at least part of the anatomical joint; and
    vi) generating a decision support material, where the determined damage to the anatomical joint is marked in at least one of the one or more damage images of the decision support material, and at least one of the one or more damage images is generated based on the obtained three-dimensional image representation of the at least part of the anatomical joint.

11. The method according to claim 10, wherein at least one of the one or more damage images is an interactive 3D model of the anatomical joint or part of it.

12. The method according to claim 10, wherein the image analysis identifies bone parts and/or cartilage parts of the joint in said at least one radiology image by the steps of:

detecting high contrast areas such as edges or contours in the radiology image; and identifying structures, such as bone and/or cartilage, in the radiology image through comparing the detected edges or contours with predefined templates.

13. The method according to claim 10, wherein damage is determined using the identified tissue parts and a selection of:

detecting an irregular shape of a contour of the at least one tissue part of the anatomical joint; or detecting that the intensity in an area within or adjacent to bone and/or cartilage parts of the anatomical joint is higher or lower than a predetermined value; or comparing at least one identified tissue part with a template representing a predefined damage pattern for an anatomical joint.

14. The method according to claim 10, wherein the radiology images and the three-dimensional image representation are associated, so that a marking made in one of the images appears in the same position in another of the images.

15. The method according to claim 10, wherein the anatomical joint is an ankle, and the damage that is determined and marked in at least one of the one or more damage images of the decision support material is related to the talus.

16. The method according to claim 10, wherein the image analysis identifies both bone parts and cartilage parts of the anatomical joint or part of it and damage is determined to both the bone parts and the cartilage parts.

17. The method according to claim 10, further comprising:

selecting a suitable implant from a predefined set of implants with varying dimensions, and/or proposing a transfer guide tool for osteochondral autograft transplantation, possibly including suitable size and/or suitable harvesting and/or implantation positions for at least one osteochondral autograft plug based on data from the radiology images and/or the three-dimensional image representation of the at least part of the anatomical joint; and visualizing the selected implant and/or the transfer guide tool and/or the suitable harvesting and/or implantation positions for at least one osteochondral autograft plug in at least one of the one or more damage images.

18. The method according to claim 10, wherein the decision support material is adapted to be used by medical staff, and includes a recommendation for a suitable treatment for repair of the determined damage.

19. A decision support material indicating damage to at least a part of an anatomical joint of a patient, wherein the decision support material comprises one or more damage images generated by the method steps of claim 10, wherein the decision support material is stored in a non-transitory computer-readable storage medium and wherein at least one of the one or more damage images is an interactive 3D model of the anatomical joint or part of the anatomical joint.

20. A non-transitory machine-readable medium on which is stored machine-readable code which, when executed by a processor, controls the processor to perform the method steps of claim 10.

* * * * *

UNITED STATES PATENT AND TRADEMARK OFFICE
CERTIFICATE OF CORRECTION

PATENT NO. : 11,282,195 B2
APPLICATION NO. : 16/886650
DATED : March 22, 2022
INVENTOR(S) : Richard Lilliestråle et al.

It is certified that error appears in the above-identified patent and that said Letters Patent is hereby corrected as shown below:

On the Title Page

Item (72) Inventors:
"Richard Lilliestråle, Stockholm (SE);
Anders Karlsson, Kâvlinge (SE);
Jeanette Spångberg, Skogäs (SE);
Nina Bake, Lidingö (SE)"

Should read as:
--Richard Lilliestråle, Stockholm (SE);
Anders Karlsson, Kävlinge (SE);
Jeanette Spångberg, Skogås (SE);
Nina Bake, Lidingö (SE)--

Signed and Sealed this
Ninth Day of August, 2022

Katherine Kelly Vidal
*Director of the United States Patent and Trademark Office*